(12) United States Patent
Kaiser

(10) Patent No.: US 7,494,629 B2
(45) Date of Patent: Feb. 24, 2009

(54) DECONTAMINATION SYSTEM

(75) Inventor: Robert Kaiser, Winchester, MA (US)

(73) Assignee: Entropic Systems, Inc., Winchester, MA (US)

( * ) Notice: Subject to any disclaimer, the term of this patent is extended or adjusted under 35 U.S.C. 154(b) by 0 days.

(21) Appl. No.: 11/451,294

(22) Filed: Jun. 12, 2006

(65) Prior Publication Data

US 2009/0010824 A1   Jan. 8, 2009

Related U.S. Application Data

(63) Continuation-in-part of application No. 10/154,428, filed on May 23, 2002, now abandoned.

(60) Provisional application No. 60/293,016, filed on May 23, 2001.

(51) Int. Cl.
*A61L 2/18* (2006.01)

(52) U.S. Cl. .................. 422/292; 422/28; 442/122; 442/179

(58) Field of Classification Search .......... 442/122, 442/179; 15/104.93; 422/28, 292
See application file for complete search history.

(56) References Cited

U.S. PATENT DOCUMENTS

| | | | |
|---|---|---|---|
| 2,933,453 A | | 4/1960 | Burks, Jr. |
| 3,874,649 A | | 4/1975 | Teng et al. |
| 3,874,849 A | | 4/1975 | Teng et al. |
| 4,496,359 A | * | 1/1985 | Pigneul ............... 604/387 |
| 4,842,746 A | | 6/1989 | Fowler et al. |
| 4,847,089 A | | 7/1989 | Kramer et al. |
| 4,850,729 A | | 7/1989 | Kramer et al. |
| 4,928,681 A | | 5/1990 | Langston et al. |
| 5,079,792 A | * | 1/1992 | D'Haen ............... 15/227 |
| 5,230,960 A | * | 7/1993 | Iizuka ............... 428/408 |
| 5,264,044 A | | 11/1993 | Li |
| 5,695,775 A | * | 12/1997 | von Blucher et al. ....... 424/405 |
| 5,750,488 A | * | 5/1998 | Haskell et al. ............ 510/412 |
| 5,938,858 A | | 8/1999 | Yokoyama et al. |

(Continued)

FOREIGN PATENT DOCUMENTS

BE   903622 A   3/1986

(Continued)

OTHER PUBLICATIONS

Yam, C.S. et al., Abstract of "Enhanced Removal of Radioactive Particles from Circuit Boards by Fluorinated Surfactant Solutions," Proceedings of the Annual Meeting of the Adhesion Society, 1995, 18th, pp. 62-65.

(Continued)

*Primary Examiner*—Sean E Conley
(74) *Attorney, Agent, or Firm*—Cesari and McKenna LLP

(57) ABSTRACT

A decontamination pad includes an adsorptive/absorptive knitted activated-carbon layer exposed on a first surface, an activated-carbon fabric attached to the other surface of the knitted layer and backed up an impermeable layer. The activated carbon is saturated with a non-hazardous CWA decontamination solvent as nonspecific means of decontaminating equipment and open-wounds is provided. The pad is packaged in a sealed, disposable plastic packet. The pad is thus a simple and immediate means of personal decontamination by applying the exposed surface of the knitted layer to the surface to be decontaminated.

15 Claims, 10 Drawing Sheets

U.S. PATENT DOCUMENTS

| | | | |
|---|---|---|---|
| 6,053,952 | A | 4/2000 | Kaiser |
| 6,156,407 | A | 12/2000 | Neubauer et al. |
| 6,375,976 | B1 | 4/2002 | Roden et al. |

FOREIGN PATENT DOCUMENTS

| | | |
|---|---|---|
| EP | 0053936 B1 | 4/1989 |
| JP | 09111653 A | 4/1997 |

OTHER PUBLICATIONS

"Decontamination Kit, Individual Equipment: M295", SBC COM online, http://sbccom.apgeo.army.mil/products/m295.htm, May 2, 2000, 2 pages.

"M291 Skin Decontamination Kit", SBC COM online, http://sbccom.apgeo.army.mil/products/m291.htm, May 11, 2000, 1 page.

Dr. Stephen Thomas, Bruce Fisher, Paul Fram, & Dr Mike Waring, "Odour Absorbing Dressings: A comparative laboratory study", World Wide Wounds—The Electronic journal of wound management practice, http://smtl.co.uk/world-Wide-Wounds/1...-Dressings/odour-absorbing-dressings.html, Jul. 3, 1998, 11 pages.

"Sorbent Decontamination Systems (SDS)", SBC COM online, http://sbccom.apgeo.army.mil/RDA/sds/index.htm, Sep. 19, 2000, 4 pages.

"Sorbent Decontamination System, XM100", SBC COM online, http://sbccom.apgeo.army.mil/products/sds.htm, Sep. 19, 2000, 1 page.

Peter Zvirble & Albert A. Koadritner, "Studies On Skin Decontamination", Chemical Corps Medical Laboratories Research Report, Jun. 1953, 17 pages.

"Wound and Skin Care", CarboFlex, http://www.convatec.com/wound2/whatsnew/carbofl.htm, Nov. 9, 1999, pp. 1-2.

"S.M.T.L. Dressing Data Cards," http://www.smtl.co.uk/WMPRC/DataCards/HTML/, Dec. 16, 1997, 11 pages.

C. Van Hooidonk, B.I. Ceulen, J. Bock, and J. Van Genderen, "CW Agents and the Skin Penetration and Decontamination", Proc. Int. Symp. Protection Against Chemical Warfare Agents, Stockholm, Sweden, Jun. 6, 1983, pp. 153-160.

Dr. Ming-Houng (Albert) Chang, Dr. Alex Ciegler, Dr. Roy Crochet, "A Survey and Evaluation of Chemical Warfare Agent-decontaminants and Decontamination" Defense Information Systems Agency, U.S. Department of Defense, Oct. 15, 1984, 82 pages.

Albert M.H. Chang, PH.D. and Alex Ciegler, PH.D "Chemical Warfare: Part I: Chemical Decontamination" vol. 1, No. 4, Oct. 1984, pp. 59-65.

"Health Service Support In a Nuclear, Biological, and Chemical Environment" Field Manual FM 9-10-7, Headquarters, Department of the Army, Nov. 9, 1999, 19 pages.

"Thermal Management Fluids and Services", 3M Fluorinert Electronic Liquid, 3M Novec Engineered Fluids, Jun. 2000, 4 pages.

"A High-Performance Heat Transfer Fluid with Favorable Environment Properties" 3M Novec Engineered Fluid HFE-750, Jun. 2000, 11 pages.

Phillip Tuma, Lew Tousignant, "Reducing Emissions of PFC Head Transfer Fluids" EHS Challenges and Analytical Methodologies session at the SEMI Technical Symposium, Jul. 16, 8 pages.

\* cited by examiner

CONTAMINANT REMOVAL FROM PORK SKIN BY INCREMENTAL WIPES
WITH A LIQUID SOAKED COTTON PAD

| RUN No | F-06 | F-07 | F-08 | F-09 | F-10 | F-11 | F-12 | F-13 |
|---|---|---|---|---|---|---|---|---|
| SIMULANT | NEAT | NEAT | NEAT | THICKENED | THICKENED | THICKENED | THICKENED | THICKENED |
| INITIAL CONTAMINATION LEVEL, gr./ | 2.1 | 2.1 | 2.1 | 1.3 | 1.3 | 1.3 | 1.3 | 1.3 |
| LIQUID IN WIPE | HFE-7200 | HFE-7100 | NONE | HFE-7100 | HFE-7200 | NONE | BLEACH | WATER |
| PERCENT CONTAMINANT REMAINING (*) | | | | | | | | |
| AFTER WIPE 1 | 39.1% | 78.2% | 97.2% | 94.0% | 71.8% | 81.3% | 61.3% | 92.2% |
| AFTER WIPE 2 | 44.9% | 59.0% | 82.0% | 95.5% | 47.1% | 65.2% | 36.5% | 78.1% |
| AFTER WIPE 3 | 24.8% | 44.4% | 83.7% | 88.7% | 41.0% | 61.4% | 31.3% | 77.9% |
| AFTER RUB 1 | 0.1% | 10.4% | 9.7% | 34.5% | 11.8% | 5.6% | 0.73% | 8.4% |

* BASED ON SURFACE AREA UNDER HISTOGRAM FOR LIGHT INTENSITY VALUES > 100 WITH OUT AUTO-CONTRAST

FIG. 6

PHOTOMICROGRAPH OF ACTIVATED CARBON KNITTED FABRIC 1 cm

PHOTOMICROGRAPH OF ACTIVATED CARBON WOVEN FABRIC 1 cm

PHOTOMICROGRAPH OF ACTIVATED CARBON FELT

DECONTAMINATION SYSTEM

CROSS-REFERENCE TO RELATED APPLICATIONS

The present application claims the benefit of U.S. Provisional Patent Application Ser. No. 60/293,016, which was filed on May 23, 2001, by Robert Kaiser for a Decontamination System and Methods of Decontamination and is hereby incorporated by reference.

The present application is a continuation-in-part of application Ser. No. 10/154,428 entitled DECONTAMINATION SYSTEM AND METHOD OF DECONTAMINATION filed May 23, 2002 now abandoned.

BACKGROUND OF THE INVENTION

1. Field of the Invention

The invention relates to materials and methods for decontamination of items and persons contaminated with chemical and biological agents, and more particularly to decontamination of open wounds.

2. Background Information

The capability to decontaminate (preferably neutralize, but at least remove) chemical and biological agents from human skin, or from articles handled by humans, and in particular from open-wounds of casualties is extremely valuable to the military. This capability will increase the safety and survivability of casualties and personnel in the course of medical treatment of casualties in an environment that is contaminated with chemical and/or biological threat agents, and will allow medical personnel to more readily treat casualties in a safe and effective manner.

The level of decontamination required is established by the toxicity level of the agent involved. The percutaneous values for 50% percentile lethal dose for the major Chemical Warfare Agents (CWA) are as follows:

| Agent | LD 50 (skin), mg/kg |
|---|---|
| HD (Mustard) | 100 |
| GB (Sarin) | 24.3 |
| GA | 9.3 |
| GD (Soman) | 5.0 |
| VX (Nerve Agent) | 0.14 (per minute) |

The above values have to be converted into surface concentration values used to quantify surface decontamination procedures. This is done in Table 1-1.

TABLE 1-1

Correlation Between Surface Contamination and Contaminant Dose Levels

| Surface Contamination | Patient Contamination Level g/patient | | Contaminant Dose mg/kg (1) | |
|---|---|---|---|---|
| Level, g/m$^2$ | Worst (2) | Nominal (3) | Worst (2) | Nominal (3) |
| 10 | 20 | 0.2 | 286 | 2.86 |
| 1 | 2 | 0.02 | 29 | 0.29 |
| 0.1 | 0.2 | 0.002 | 2.9 | 0.029 |
| 0.01 | 0.02 | 0.0002 | 0.29 | 0.0029 |
| 0.001 | 0.002 | 0.00002 | 0.03 | 0.0003 |

(1) Assumes a Patient Weight of 70 kg (154 lbs)
(2) Assumes total skin coverage = 2 m$^2$ of contaminated area
(3) Assumes 200 cm$^2$ of contaminated area Without decontamination, any victim whose whole body was exposed to any CWA agent at the NATO standard load of 10 g/m$^2$ without receiving immediate decontamination would be doomed. Reducing the dose level equal to 10% of the LD50 value, significantly increases survivability; so patients decontaminated to a level of 0.01 gr./m$^2$ would likely survive after having been exposed to any of the agents listed above, except for VX. In the case of VX, the residual surface contamination level should be less than 0.001 gr./m$^2$.

The decontamination of a combatant with an open-wound is a multi-faceted problem that involves both personal decontamination by the wounded individual and casualty decontamination by medical support personnel.

Decontamination after any chemical exposure is most effective when performed within the first minute or two after exposure. This can be performed by the victim or by a squad mate, if one is available. Early action by the patient to decontaminate himself can make the difference between survival (or minimal injury) or death (or severe injury).

Presently, there are no effective personal means of open-wound decontamination. The standard M258A and M291 skin decontamination kits, which would be issued to the combatant, are both specifically contra-indicated for decontamination of open-wounds. The present recommended options for open wound decontamination are irrigation with water, saline, or dilute hypochlorite solution, none of which, other than water, a combatant is likely to possess when wounded.

Walter Reed Army Institute of Research (WRAIR) has demonstrated that a combination of cholinesterase (ChE) pre-treatment with an oxime is an effective measure against nerve agents. WRAIR is currently developing sponges in which ChE is covalently linked to a polyurethane matrix. The ChE sponges retained their catalytic activity under conditions of temperature, time and drying where the native soluble enzyme would rapidly denature, and can be reused in conjunction with oximes many times. Such ChE sponges, in the presence of oxime, repeatedly detoxified organophosphates (OP) such as DFP (diisopropyl fluorophosphate) and MEPQ (7-(methylethoxyphosphinyloxy)-1-methylquinolinium iodide). These sponges have the potential of providing a simple wipe method means of detoxifying or decontaminating a wide range of OP-contaminated surfaces. If and when such sponges were included in a skin decontamination kit, they would be expected to provide a means of personal protection that would be safe to use on open-wounds as well as unbroken skin.

While effective against nerve gases, these sponges would have little effect against chemical warfare agents (CWA) that are not OPs, such as mustard (Agent HD). No generally effective method of personal decontamination of an open-wound currently exists.

Decontamination of chemical casualties is an enormous task. The process requires dedication of both large numbers of personnel and large amounts of time. Even with appropriate planning and training, decontamination of casualties demands a significant contribution of resources.

Casualties or other persons entering a medical unit after experiencing a chemical attack are presumed contaminated. In a contaminated environment, casualties ideally enter a medical treatment facility through the contaminated casualty receiving area. The purpose of this area is to provide for the removal of chemical contamination from the casualty before he enters the clean medical treatment facility and as a result maintain a contamination free treatment area. The components of this receiving area are: the arrival point, the triage area, the emergency treatment area, the decontamination area(s), and the "hot line" separating the decontamination and medical treatment areas.

The initial management of a litter casualty contaminated with chemical agents will require removal of mission-oriented gear and its decontamination. This can be done either by physical or chemical removal. Physical removal methods include: wiping with a wet or dry piece of cloth, scraping with a tongue depressor, flushing or flooding the contaminated skin with water or aqueous solutions that can remove or dilute significant amounts of agent, adsorption by granular materials, such as M 291 resin.

Chemical removal methods include soap and water cleansing, oxidation and hydrolysis.

Dilute hypochlorite solution has been commonly used as a means of decontamination that provides both physical and chemical means of removal. Both oxidation and hydrolysis occur in alkaline hypochlorite solution. Within the context of casualty decontamination, it has been standard operating procedure to use 5% hypochlorite solution to decontaminate clothing and equipment and 0.5% hypochlorite solution to decontaminate skin. It was contraindicated for the eye and irrigation of the abdomen, and not recommended for brain and spinal cord injuries. Recent studies with rabbits contaminated with agent GB, indicate that the mortality rate of contaminated rabbits decontaminated with sodium hypochlorite solution is higher than that of control rabbits that were not decontaminated. They also demonstrated that decontaminating with water reduced the mortality rate. Use of dilute hypochlorite solutions for the decontamination of personnel may therefore be contra-indicated.

All military treatment facilities (MTFs) should be prepared to receive mass casualties caused by exposure to chemical agents. A mass casualty situation exists when the number and type of casualties exceed the local medical support capabilities for their care. If the unit follows standard operational procedures (SOPs), an overwhelming backlog of work will rapidly accumulate, since only a limited number of personnel can be assigned to perform decontamination at an MTF. Such backlogs can result in avoidable loss of life and limb with suffering.

To reduce such backlogs, either the number of people or the time required to perform the decontamination will preferably be reduced. While this situation may be improved by the development of improved open-wound decontamination methods, such as the ones discussed in the personal decontamination section above, they may not have significant or sufficient impact on the time required for casualty decontamination. The decontamination protocols now used require large numbers of individual steps both undressing and decontaminating the patient. Decontamination is performed by incremental wiping with wipes from the M 291 and M258A kits, or irrigating with 0.5% hypochlorite from a wash bottle at various levels of disrobing. This is inherently a slow process. If a number of the present steps could be combined, or a more rapid means of agent removal be introduced, it should be possible to reduce the time needed to decontaminate a patient. The logistics of casualty decontamination should be reviewed and alternate methods of patient management and decontamination should be examined.

SUMMARY OF THE INVENTION

A decontamination system including an absorptive/adsorptive activated carbon felt pad saturated with a non-hazardous CWA decontamination solvent as nonspecific means of decontaminating equipment and open-wounds is provided. The entire system preferably includes an absorbent pad and decontamination fluid in a sealed, disposable plastic packet. The system is thus a simple and immediate means of personal decontamination. The decontamination fluid and the absorbent pads are non-hazardous, nontoxic, and nonflammable. The system is thus safe, and able to readily meet with FDA approval. The system is small and easily carried in a field pack or other means and can be safely disposed of after use. The same system is also useable at casualty receiving stations to decontaminate patients and/or equipment.

The decontamination system has the ability to absorb CWA into a non-hazardous fluid, and the ability to adsorb CWA from the fluid onto a solid adsorbent.

BRIEF DESCRIPTION OF THE DRAWINGS

The detailed description of an illustrative embodiment below refers to the accompanying drawings, of which:

FIG. 5-1 is a graph illustrating the adsorption of decontamination fluids onto a substrate over time;

FIG. 5-2 is a graph illustrating the adsorption of agent from various decontamination fluids over time;

FIG. 6 is a table showing the results of wiping contaminated substrates with various wipes;

DETAILED DESCRIPTION OF AN ILLUSTRATIVE EMBODIMENT

Figure 1:
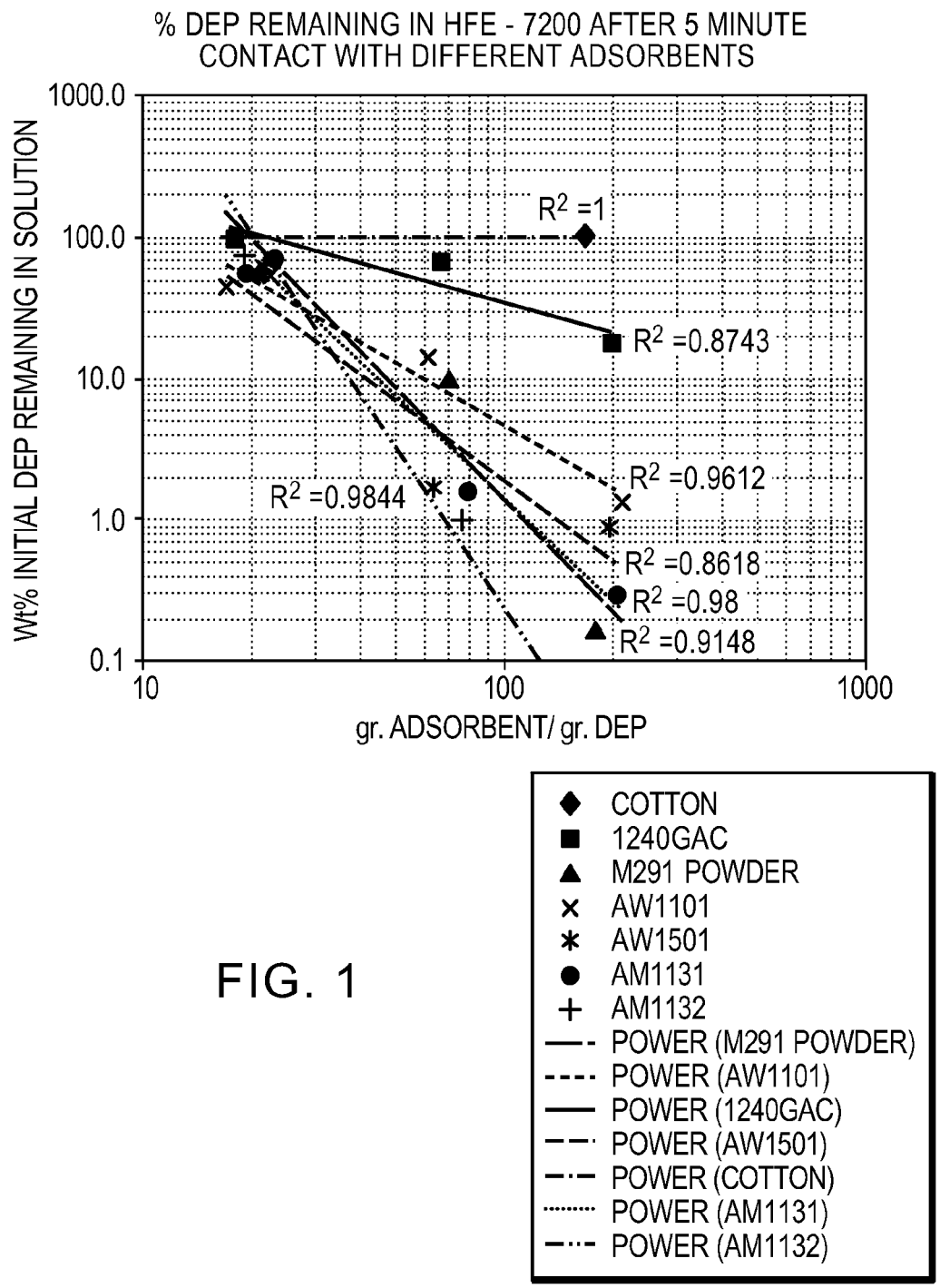
FIG. 1 is a graph illustrating the adsorption of a CWA simulant onto different materials.

One illustrative embodiment of the decontamination system includes an absorption/adsorptive pad system saturated with a decontamination fluid. The decontamination fluid preferably has the ability to dissolve the contaminant and is compatible with the substrate being cleaned, namely it preferably is be safe and not alter the physical or chemical properties of the substrate being cleaned.

The decontamination liquid for CWA decontamination preferably meets the following criteria:

a. It is compatible with a wide range of sensitive equipment—i.e. the performance of electronic and optical equipment is not affected by immersion in the liquid.

b. The principal chemical warfare agents (CWA) of concern are sufficiently soluble in the decontamination liquid for it to be an effective decontamination medium.

c. The principal chemical warfare agents (CWAs) of concern can be effectively removed from the decontamination liquid. Preferably, when agent contaminated decontamination liquid is passed through a purification module, the agent is quantitatively removed from the decontamination liquid, resulting in contaminant free decontamination liquid that can be recycled and reused.

d. It is nonflammable, nontoxic, and environmentally acceptable.

Table 1 below lists the properties of decontamination liquids compared to the properties of Freon TF. These materials have been shown to be effective decontamination fluids.

TABLE 1

Properties of Decontamination Solvents

| | Solvent | | | |
|---|---|---|---|---|
| | Vertrel-XF [HFC-43-10] | HFE-7100 | HFE-7200 | HFE-7500 |
| Chemical Formula | C5F10H2 | C5F9H3O | C6F9H5O | C9F15H5O |
| Supplier | Du Pont | 3M Co. | 3M Co. | 3M Co. |
| Molecular Weight | 252 | 250 | 264 | 414 |
| Boiling Point, °C. | 54 | 61 | 76 | 130 |
| Freezing Point, °C. | −80 | −135 | −138 | −100 |
| Heat of Vaporization, cal/g @ bp | 31 | 30 | 30 | 21 |
| Specific Heat, cal/g @ 25° C. | 0.27 | 0.28 | 0.29 | 0.27 |
| Specific Gravity (H20 = 1) | 1.58 | 1.52 | 1.43 | 1.61 |
| Viscosity, cp @ 25° C. | 0.67 | 0.61 | 0.61 | 1.24 |
| Surface Tension, dynes/cm @ 25° C. | 14.1 | 13.6 | 13.6 | 16.2 |
| Vapor Pressure, mm Hg @ 25° C. | 226 | 202 | 109 | 16 |
| Solubility of | | | | |
| Water in Solvent, ppm | 490 | 95 | 92 | 45 |
| Solvent in Water, ppm | 140 | <12 | 20 | <6 |
| Hildebrand Solubility Parameter, MPa^0.5 | 13.8 | 12.4 | 12.9 | 11.9 |
| VOC, lbs/lb | 0 | 0 | 0 | 0 |
| Ozone Depletion Potential (CFC-11 = 1.0) | 0 | 0 | 0 | 0 |
| Global Warming Potential (100 yr ITH) | 1700 | 320 | 55 | 210 |
| Atmospheric Lifetime, yrs | 17.1 | 4.1 | 0.8 | 2.5 |
| Flashpoint, °C. | None | None | None | None |
| Flammability Range in Air, % | None | None | 2.4-12.4% | 2.4-12.4% |
| Exposure Guidelines, 8 hr TWA, ppm | 200 | 750 | 200 | 200 |

The properties of four major CWAs are shown in Table 2 below:

TABLE 2

Physical-Chemical Properties of Chemical Warfare Agents Examined

| | Agent | | | |
|---|---|---|---|---|
| | HD | GB | GD | VX |
| Chemical Formula | C4H8C12S | C4H10FO2P | C7H16FO2P | C11H26NO2PS |
| Molecular Weight | 159 | 140 | 182 | 267 |
| Specific Gravity @ 25° C. | 1.27 | 1.092 | 1.025 | 1.011 |
| Viscosity, cs @ | 4.07 | 1.28 | 3.10 | 9.96 |
| Temperature, °C. | 20 | 25 | 25 | 25 |
| Surface Tension @ 20° C., dynes/cm | 43.2 | 26.5 | 24.5 | 32 |
| Freezing Point, °C. | 14.5 | −56 | −42 | −50 |
| Boiling Point, °C. | 217.5 | 158 | 198 | 298 |
| Vapor Pressure @ | | | | |
| 20° C. | 0.069 | | | |
| 25° C. | 0.11 | 2.9 | 0.4 | 0.00063 |
| 60° C. | 1.7 | 18 | 3.2 | 0.015 |
| Hildebrand Solubility Parameter, MPa^1/2 | 21.4 | 17.6 | 16.9 | 18.2 |
| Solubility in Water @ RT, gr/100 gr | 0.92 | Miscible | 2.1 | 3.0 |
| LD 50 (skin), mg/kg | 100 | 24.3 | 5 | 0.14 |
| LD 50 (oral), mg/kg | 0.7 | | | |
| Toxicity Limit, 8-hr TWA, mg/m3 | 0.003 | 0.0001 | 0.00003 | 0.00001 |
| Flash Point, °C. | 105 | >280 | 121 | 159 |

The Hildebrand Solubility Parameter is often used as a predictor of mixing ability (solubility, compatibility) of two or more components, criteria b, above. For liquids at room temperature, this parameter ranges from a value of about 12 Mpa$^{1/2}$ for perfluoroalkanes to 47.9 Mpa$^{1/2}$ for water. The value of this parameter increases with the polarity and hydrogen-bonding capability of the material. The Hildebrand solubility parameter is a numerical expression of the chemical rule-of-thumb that similar compounds are mutually soluble (i.e. "like likes like"). Two materials that have similar solubility parameters (i.e. differ by less than 50%) tend to be mutually soluble, where as materials that have significantly different solubility parameters usually are immiscible (such as water and perfluoroheptane). The estimated values of the Hildebrand solubility parameter for the CWA listed in Table 2 range from 16.9 Mpa$^{1/2}$ for GD to 21.4 Mpa$^{1/2}$ for HD. These agents are soluble in organic solvents and, except for GB, relatively insoluble in water.

The decontamination liquid, therefore, preferably has a Hildebrand Solubility Parameter which differs by less than 50% of the CWA of interest. It is also preferred that the decontamination liquid not have an identical Hildebrand solubility parameter so that the CWA can be later removed from the decontamination liquid.

Nerve agents tested were miscible in all the solvent systems tested, miscibility being defined as complete mutual solubility of equal volumes of agent and solvent.

The composition of the solvent had a significant effect on the removal of dissolved agent by adsorption on activated carbon. Specific agent loading on is presented in Table 4. In general, the higher the solubility of the agent in the solvent, the more difficult it became to remove the agent from solution by activated carbon. While differences were noted between agents, the ability of activated carbon to pull agent out of solution was higher for a "poor" solvent than for a good solvent.

HFCs are somewhat poorer solvents for hydrocarbon base soils than CFC-113. In particular, while HFCs exhibit significant solvency for oxygenated compounds such as esters, ketones, ethers, and ether alcohols and lower molecular weight aliphatic hydrocarbons, many heavier organic soils, such as viscous oils, as well as polar or aqueous base compounds, are not soluble in Vertrel-XF or HFE-7100.

Since the physical chemical characteristics of the chemical warfare agents (CWA) of principal concern (mustard (HD) and the nerve agents (GA, GB, GD, and VX) are similar to those of esters (esters are often used as harmless agent simulants) (compare Table 1, Table 2), the solubility of these CWA in HFCs and HFEs is sufficiently high to allow contaminated parts to be decontaminated by immersion or wiping in these solvents. If the solubility was not sufficiently high, the performance characteristics of the HFCs/HFEs could be improved by the addition of functional additives or co-solvents that would not degrade the inherent safety and environmental characteristics of these materials.

The major limitation to adsorption of CWA is the presence of solutes in the used decontamination fluid that might interfere with the adsorption of the CWA also dissolved in the solution. A lesser problem is the coadsorption of non-toxic contaminants on the activated carbon granules, which would reduce adsorption capacity for CWA.

EXPERIMENTAL METHOD AND RESULTS

The results of solubility experiments are summarized in Table 3. The results of the adsorption results are summarized in Table 4.

TABLE 3

Solubility of Chemical Agents in Solvents of Interest

|  | GB | GD | HD |  |
|---|---|---|---|---|
| Vertrel-XF | M (RT) | M (RT) | 8% (40° C.) | M (RT) |
| HFE-7100 | M (RT) | M (RT) | 8% (40° C.) | M (RT) |
| HFE-7200 | M (RT) | M (RT) | 8% (40° C.) | M (RT) |
| CHP | M (RT) | M (RT) | M (RT) | M (RT) |

TABLE 4

D. Chemical Agent Removal From Solvents of Interest by Activated Carbon

|  | GB | GD | HD |
|---|---|---|---|
| Vertrel XF | 28% | 53% | 100% |
| HFE-7100 | 52% | 68% | 96% |
| HFE-7200 | 69% | 76% | 92% |
| CHP | 0% | 0.75% | 7.9% |

Among the CWA, agents GB and GD were more difficult to remove by adsorption than agents HD and VX. The tendency for HD to adsorb readily is not surprising in that it was the least soluble of all the agents tested in the candidate liquids. The ability to remove agent VX by adsorption came as a favorable surprise because it dissolved so readily in all liquids tested.

Agents GB and GD were the most sensitive to solvent composition. There was essentially no adsorption of either agent from solution in Vertrel KCD 9572 or in cyclohexyl pyrrolidone. There was significantly less adsorption from solution in Vertrel-XF, with or without isopropanol, than from HFE-7100 or HFE-7200.

TABLE 5

Specific Adsorption of Chemical Agents on Activated Carbon from Solvents of Interest

|  | GB | GD | HD | VX |
|---|---|---|---|---|
|  | mg of agent per gr of AC | | | |
| Vertrel XF | 0.052 | 0.114 | >0.275 | >0.19 |
| HFE-7100 | 0.241 | 0.408 | 0.282 | >0.39 |
| HFE-7200 | 0.314 | 0.45 | 0.139 | >0.38 |
| CHP | 0 | 0.005 | 0.135 | NA |

Surprisingly, the presence of isopropanol in Vertrel-XF had little or no effect on the level of agent adsorption on activated carbon A second key advantage of sensitive equipment decontamination liquid is that it is compatible with the equipment being decontaminated. Contact with the decontamination liquid during a decontamination cycle can not affect the performance characteristics of the sensitive equipment being decontaminated. The decontamination process should not change either the appearance of the object or its functional (i.e. electrical, electronic, or optical) performance.

HFE-7100 and HFE-7200 were compatible with all materials that we would be likely to be used in the construction of sensitive equipment.

Toxicology studies performed by 3M have shown these hydrofluoroethers to be low in overall toxicity. These liquids are practically non-irritating to the eyes and skin, not skin sensitizers, are not mutagens or developmental toxins not toxic by ingestion (>5 g/kg) and practically non-toxic through inhalation (LD50>92,000 ppm over 4 hrs). Liquids of this class are believed to be less damaging to the body, including open wounds, than the dilute (0.5%) bleach solution previously used.

Vertex XF has also been used advantageously.

A pad system is preferably formed of at least one activated carbon layer. The activated carbon forming the layer has a surface area between about 100 to 1500 $m^2/g$ or more. Preferably, the activated carbon layer is needle punched non-woven felt, non-shedding and can absorb at least about 5 g solvent/g fabric, and more preferably about 15 g solvent/g fabric.

Chemical agents (GB, GD, VX, and HD), as well as diethylphthalate (DEP), which was used as a VX simulant, are removed from the contamination by adsorption on activated carbon granules. The degree of removal is dependent upon several factors including agent concentration, surface area per gram of activated carbon, and the equilibrium between the adsorbed agent and the agent in solution.

Several different fabrics were tested by observing the adsorption of DEP from solution in HFE-7200 onto different substrates. These substrates include granular activated carbon, various activated carbon fiber fabrics, cotton gauze, and the active powder from the M 291 personal decontamination kit. These results are summarized in FIG. 1. A key to the abbreviations in FIG. 1 are as follows:

1240 GAC=Norit Granular Carbon, −12 mesh/+40 mesh
M 291 Powder=Powder from the M 291 decontamination kit
AW 1101=Activated Carbon Cloth (surface area 1,100 $m^2/g$) manufactured by Taiwan Carbon Company
AW1501=Activated Carbon Cloth (surface area 1,500 $m^2/g$) manufactured by Taiwan Carbon Company
AM1131=Activated Carbon Felt, (surface areal, 100 $m^2/g$), 2 mm thick, manufactured by Taiwan Carbon Company
AM 1132=Activated Carbon Felt, (surface area 1,100 $m^2/g$), 2.75 mm thick, manufactured by Taiwan Carbon Company FIG. 1 presents the percent DEP remaining in solution after five minutes of contact with the adsorbent as a function of the adsorbent/initial contaminant weight ratio. Acceptable results were obtained with an activated carbon felt (sold under the trade name AM-1132 from the Taiwan Carbon Technology Co., Ltd.) which resulted in over 99.9% removal of DEP in five minutes at a substrate to contaminant ratio of 200. Other activated carbon fiber fabrics and the powder from the M 291 kit were also effective. These, in turn, were significantly more effective than GAC 1240 granular activated carbon.

Many absorbent medical sponges, pads, and wipes are currently commercially available. These medical sorbents are typically constructed of cotton fibers and absorb liquids through capillary action. Although these types of absorbents are useful to prevent bleeding and protect a wound, they do not adsorb chemical species. This type of absorbent gauze pad may even trap CWA present on a wound.

Adsorption is an interaction between a surface and a chemical species in which the chemical species is trapped on the surface of the adsorbent. Activated carbon adsorbs agent from decontamination fluid. Adsorbent pads constructed of activated carbon fibers preferably include the following features:

1. The pad is made partially, preferably completely, from a chemical agent-adsorbing material.
2. The pad is preferably compatible with hydrofluorocarbon decontamination fluids.
3. The pad is preferably capable of absorbing decontamination fluid.
4. The pad should not be harmful to humans.
5. The pad preferably does not shed to fiber or breakdown when rubbed on skin, open-wounds or solid surfaces.
6. The pad should be storable, inexpensive, easy to use, and disposable.
7. The pad preferably has an adhesive backing, so that after initial decontamination, a second adhesive backed pad could be used as a protective bandage with inherent decontamination properties.

Figure 2:
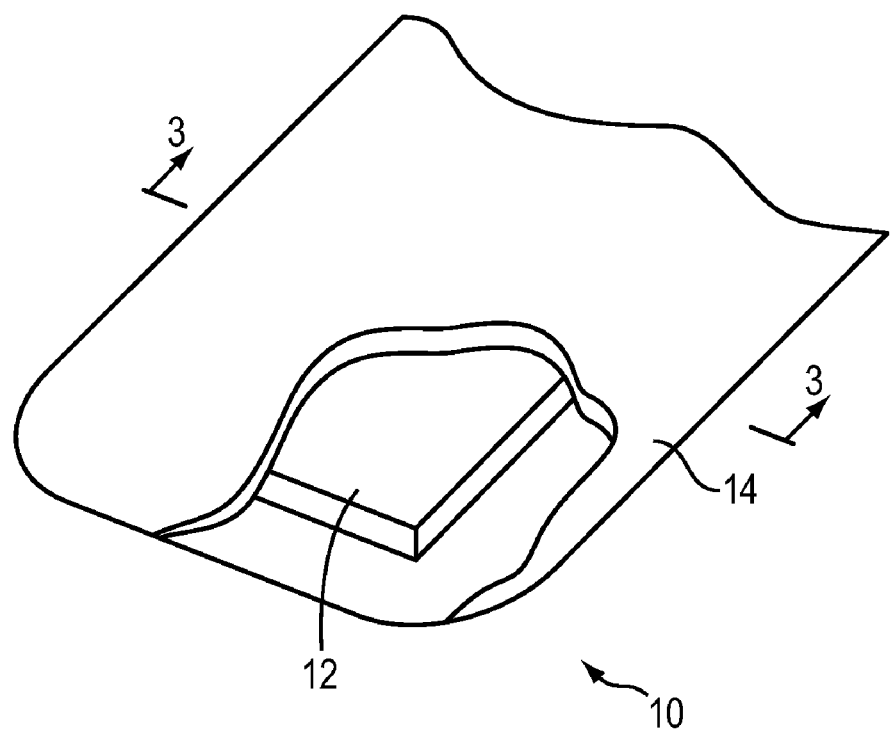
FIG. 2 is perspective view of partially broken away of a decontamination pad.
Figure 3:
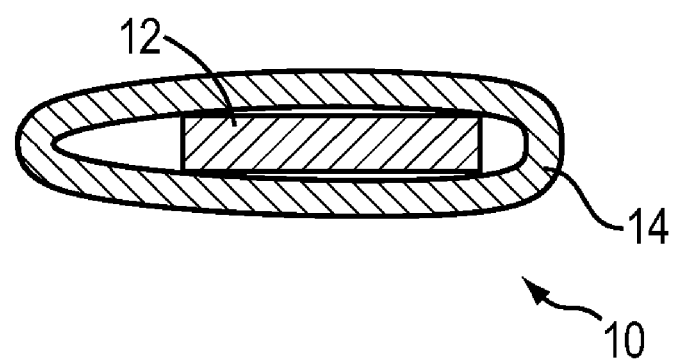
FIG. 3 is a sectional view taken generally along line 3-3 of FIG. 2.

A composite activated carbon fabric pad 10 that effectively removed DEP from the surfaces of pork skin (used as a simulant for human skin) and a pork chop (used as a simulant for an open wound) is shown in FIGS. 2 and 3. The DEP used in the experiments contained 5 wt. % of an oil soluble fluorescent dye, Try 33 (Day-Glo Company). The dye, which glows bright yellow-green when illuminated by an UV light source (364 nm wavelength), was added to facilitate the detection of trace residues on the test samples. To quantify these observations, a procedure was developed in which photographs of the substrates being processed were digitally analyzed on a personal computer, using Adobe PhotoShop as image analysis software. This procedure provides quantitative estimates of the relative amounts of fluorescent contaminant present on a surface, and is thus very useful in that it is a simple way of determining decontamination factors. The sensitivity of the procedure is of the order of 0.01 $g./m^2$.

FIGS. 2 and 3 illustrates a decontamination system which includes composite pad 10. This pad 10 includes an adsorbent layer 12, preferably a square, or other appropriately shaped layer, activated carbon felt adsorbent, such as a 3.5 inch square piece of ⅛ inch thick non-woven activated carbon felt (such as one made by Taiwan Carbon Technology Company, Ltd. under the trade name AM-1132) inserted in an envelope 14 formed of woven activated carbon fabric (Taiwan Carbon Company AW-1102) which also adsorbs. The pad 10 is saturated with decontamination fluid, such as by immersing the pad 10 in a beaker of HFE-7200, and allowed to drain until no further liquid dribbled out of the pad after it was removed from the beaker. A typical, as tested pad, weighed about 25 grams (5 grams of fabric and 20 grams of fluid)

Pads 10, such as shown in FIGS. 2 and 3, were tested on a piece of pork skin and of a pork chop that were contaminated with DEP simulant. In these tests, the pork samples were first contaminated with thickened simulant, which is more difficult to remove than neat contaminant. The initial contaminant concentration was estimated to be 1.6 $g/m^2$. The contaminated substrate was first wiped with one side of the pad 10 for a period of one minute. The wiping was performed in the photographic booth to take advantage of the UV illumination. The wiped surface was then contacted with the other side (the clean side) of the wipe. The contaminated pork sample and the pad were placed in a sealed plastic bag to prevent evaporation, for various periods of time of 15 minutes and up in duration, under a pressure of 100 kPa (76 torr). The pressure was applied by placing the plastic bag and its contents between a blood pressure cuff and a one liter bottle, and then pressurizing the cuff with compressed air to the desired pressure of 100 kPa.

Photographs with UV illumination were taken of the uncontaminated substrates, of the contaminated substrates, after wiping for one minute, and after each soak period. Examination of these photographs showed that most (over 98% by photometric analysis) of the contamination was removed by the end of the first wipe. In fact, much of the contamination appeared to have been visibly removed during the first few seconds of wiping. Most of the post-wipe residues were removed by a 15-minute soak, with only traces left after a 100-minute soak. The post-wipe residues were below the detection limit of the photometric method of analysis. It was easier to clean the relatively smooth pigskin than the pork chop, which contained bone and gristle, and thus had a more irregular surface.

The adsorbent layer 12 saturated with fluid may be used alone (without envelope 14). The fabric envelope 14 is used, however, to minimize carbon fiber shedding onto the surface being decontaminated. While there was reduced shedding with the composite pad than with AM-1132 adsorbent layer 12, alone, some carbon fiber residues were observed on the pork skin. These were barely visible in the post-treatment normal light.

The pad 10 may have one adsorbent layer 12, as shown in FIGS. 2 and 3 or a plurality of adsorbent layers 12. The envelope 14 may also be formed of a woven fabric other than activated carbon, such as inert non-adsorptive fabric like cotton or dacron.

The advantages of using solvent saturated activated carbon fabric wipes as a means of decontaminating patients with open include: efficiency, ease of use, light weight, and the pads are very effective, especially with prolonged contact. The pads require no specialized equipment and minimal set up time. A complete system includes of a small lightweight (25 gr.) pad. Additional system can be used. Patients can decontaminate themselves or one another. Use of the pads does not require specialized training. Use of the pads does not cause significant exposure to elements beyond standard removal of soiled garments. Contaminants are contained in an incinerable matrix. Waste pads are collected in a plastic bag for subsequent incineration. The number of pads dispensed depends on the number of patients that may require decontamination at a specific site. Numerous pads are easily packaged in small lightweight containers that are easy to ship and deploy. Long shelf life should be attainable with state-of-the art packaging methods. Pads of the type described are inexpensive to fabricate.

Figure 4:
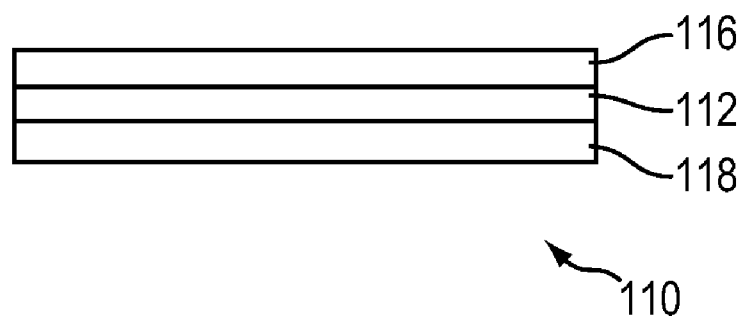
FIG. 4 is a schematic side view of an alternative decontamination system.
Figures 1, 5:
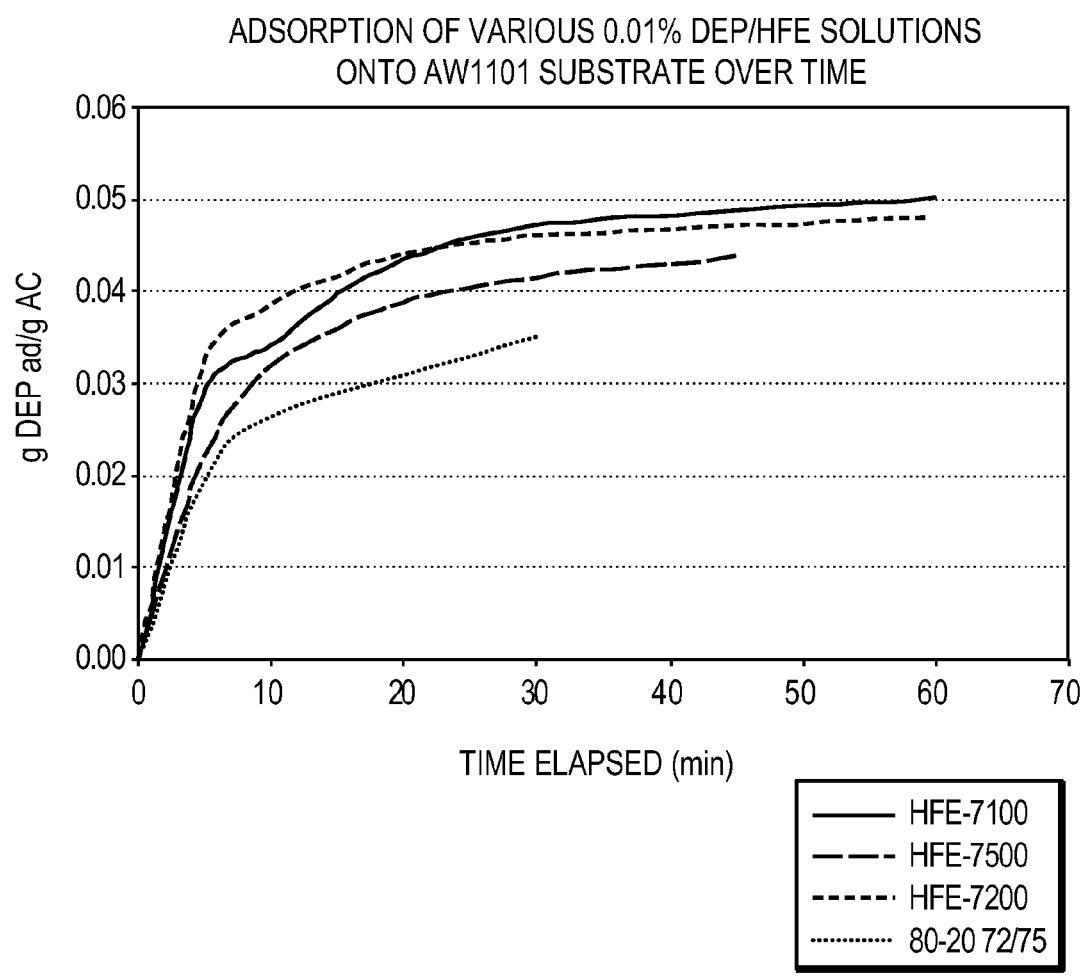
Figures 2, 5:
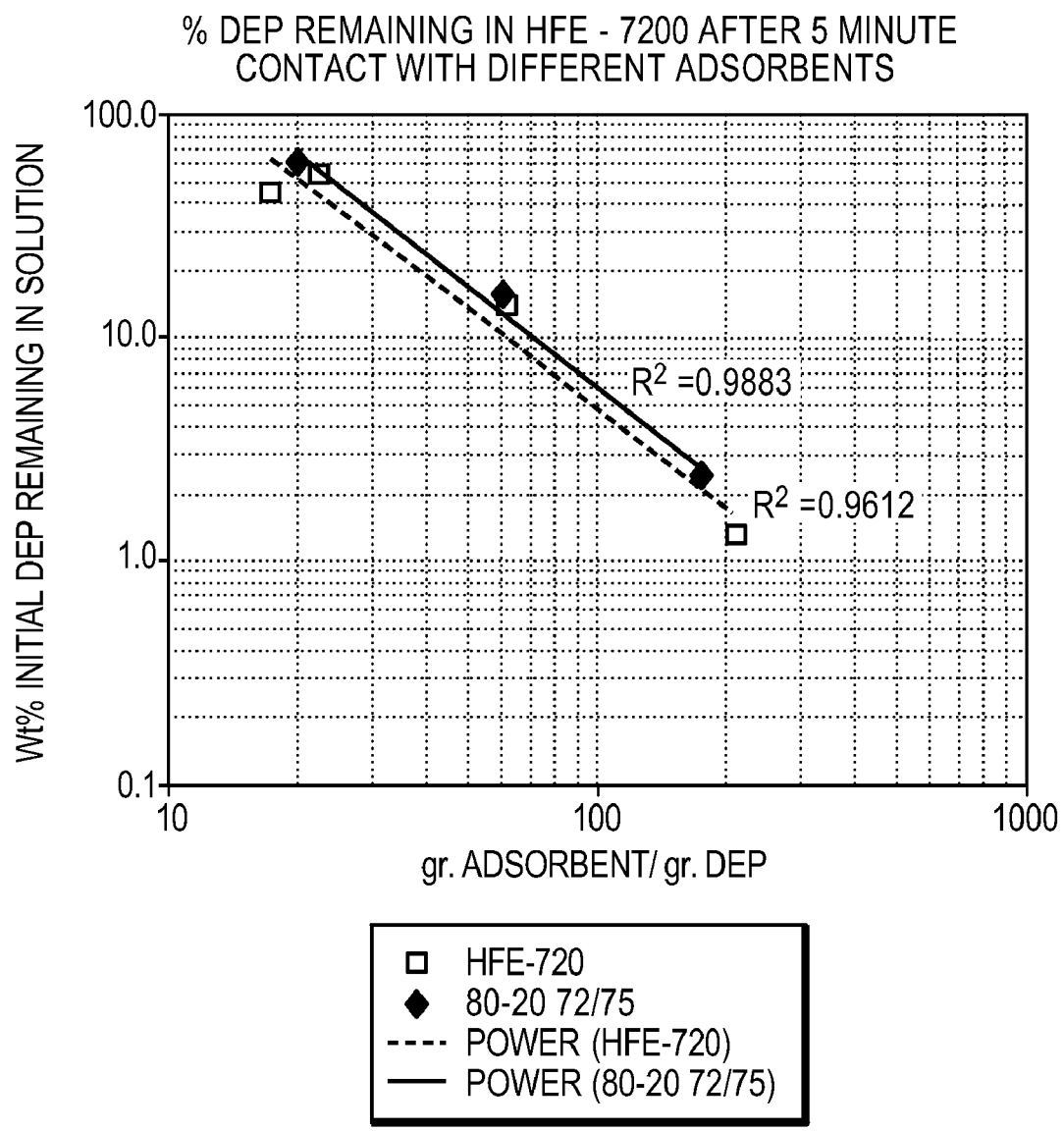

FIG. 4 schematically illustrates an alternative decontamination system. The pad 100 includes a carbon felt adsorbent layer, substantially identical to the adsorbent layer 12 of the embodiment of FIGS. 2 and 3. The adsorbent layer 112 is saturated with a decontamination fluid, as described above, and sandwiched between a barrier layer 116 and a transfer layer 118. The barrier layer is preferably non-permeable, non-porous and formed from a thin plastic film, such as polyethylene, polyvinylidene chloride (such as one sold under the trade name Saran), and aids in both preventing fluid evaporation and protecting a user from contact with the fluid. The transfer layer 118 contacts the surface to be cleaned and can be formed of an inert textile fabric, such as cotton gauze. The transfer layer 118 acts to separate and aids in preventing the adsorbed contaminants in the adsorbent layer 112 from direct contact with the body of a person or surface being treated with the pad.

In use, the non-permeable barrier layer 116 faces away from the surface being decontaminated (i.e. is an outer layer) prevents decontamination fluid from evaporating when the pad 110 is placed on top of a surface that is being decontaminated. This feature is desirable to decontaminate surfaces in which the contaminant is absorbed into the sub-surface structure of the item being decontaminated. The barrier layer 116 provides the time needed for the sorbed material to diffuse to the object surface as surface contaminant is removed.

If all the contaminant is at the surface, a non-permeable layer is not desired or needed. In this case, evaporation of solvent through the outer surface of the pad enhances the rate of decontamination by promoting mass transfer of the contaminated decontamination fluid from the surface being decontaminated to the interior of the activated carbon matrix where adsorption occurs.

In addition to the sandwich structure of the pad shown in FIG. 4, additional sandwich structure pads, each saturated with decontamination fluid, can be utilized. For example, pads may be formed in any of the following ways:

1. Layers of woven activated carbon attached to one or more layers of non-woven activated carbon containing fabric.
2. A layer of woven non-adsorptive fabric material, such as cotton, attached to one or more layers of non-woven activated carbon containing fabric.
3. One or more layers of non-woven activated carbon containing fabric attached to an impermeable plastic film, such as polyethylene or polyvinylidene chloride.
4. One or more layers of non-woven activated carbon containing fabric sandwiched between an impermeable plastic film, such as polyethylene or polyvinylidene chloride and a layer of woven activated carbon.

The layers may be attached together by stitching, by an appropriate adhesive or by any conventional means.

The availability of solvent saturated activated carbon fabric pads would satisfy a currently unmet requirement for an effective method of decontaminating patients with open wounds as well as surfaces of contaminated equipment.

The degree of removal is dependent upon several factors including agent concentration, surface area per gram of activated carbon, and the equilibrium between the adsorbed agent and the agent in solution. Activated carbon is also nonflammable, nontoxic, non-hazardous to personnel, and can be disposed of by incineration.

Although they do show some flexibility, commercially available carbon fibers and fabrics are brittle and have little mechanical integrity. When rubbed on solid surfaces, fabrics composed of brittle fibers often shed fibers on the solid surface. Shedding of chemical agent impregnated fibers is not only an undesirable result but also a potentially dangerous.

A number of foreign manufacturers make activated carbon pads (Actisorb Plus, Johnson & Johnson, Ltd. Canada; Carbonet, Smith & Nephew Medical) in which the carbon is enclosed in a flexible nylon or fibrous cellulose sheet to reduce carbon fiber and/or particle loss. These are used for wound odor control. These pads are fairly thick and do not appear to have the flexibility needed for the present intended use.

Thinner fabric enclosed pads more suitable to the needs of the present program could be made by enclosing a felt pad inside a woven fabric envelope. The felt pad would provide the required absorbing and adsorbing characteristics while external fabric, which would not necessarily have to be fabricated from activated carbon fiber, would provide mechanical integrity.

Figure 7:
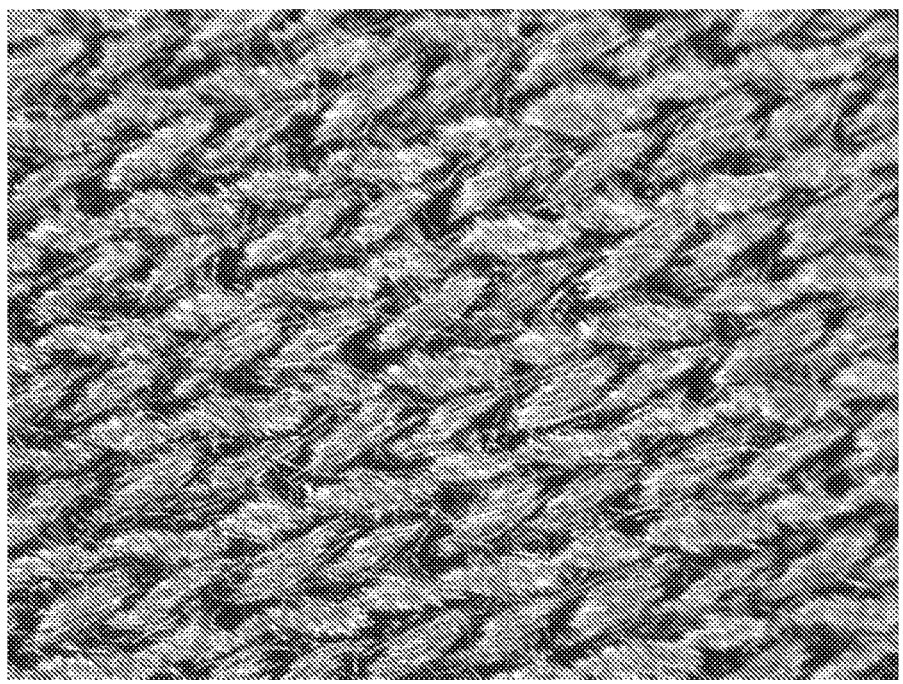
FIG. 7 is a microphotograph of the surface of a knitted activated charcoal fabric.

I have discovered that it is advantageous to construct a pad incorporating a knitted activated-charcoal outer layer instead of the woven activated-carbon layer described above. An example of a suitable knitted fabric is a knitted activated carbon fabric marketed by Calgon Carbon Corporation as Zorlfex™ 50K knitted fabric, an example of which is depicted in FIG. 7. A knitted fabric leaves substantially less material on the treated surface than woven or non-woven materials. It thus provides the advantage of having a saturated activated-carbon outer layer that has mechanical integrity and exhibits only minimal shedding of fibers on the treated surfaces.

Figure 8:
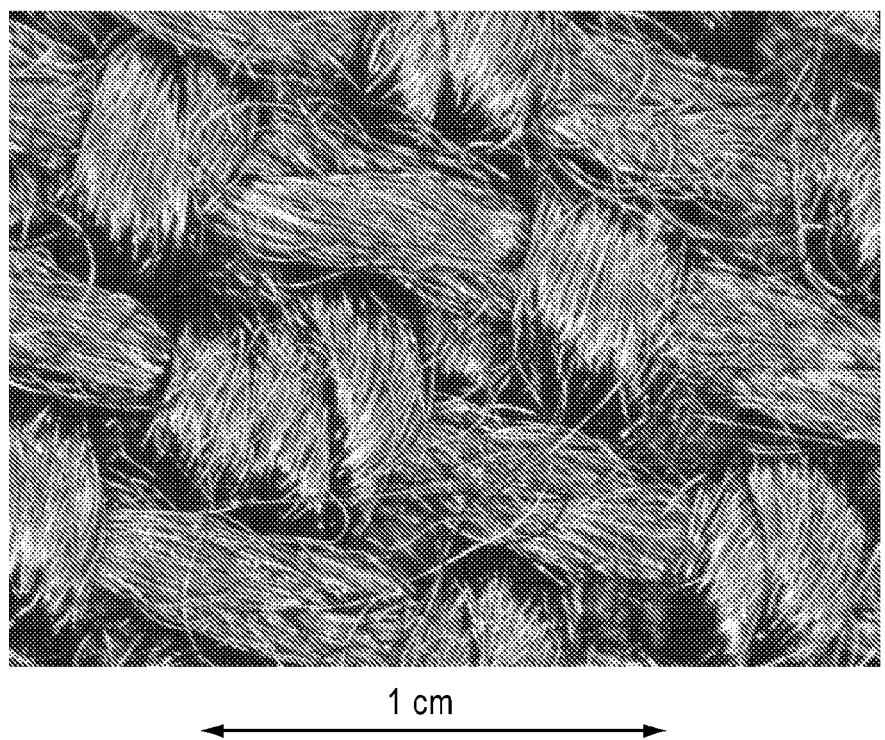
FIG. 8 is a microphotograph of the surface of a woven activated charcoal woven fabric.
Figure 9:
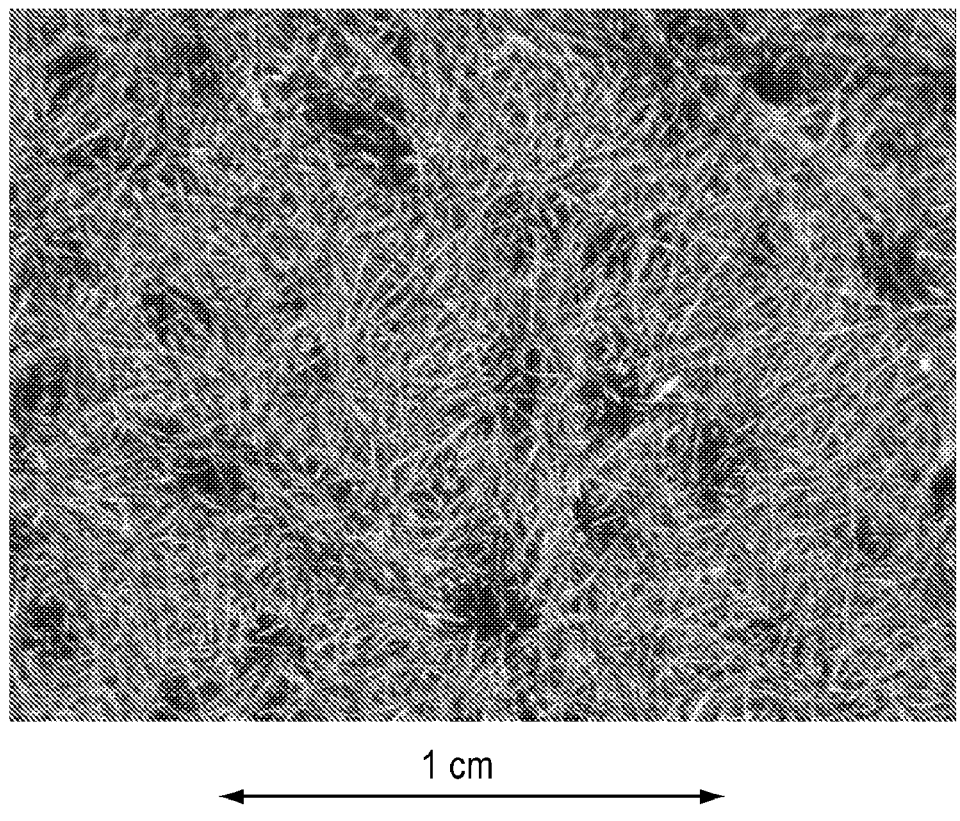
FIG. 9 is a microphotograph of the surface of a non-woven activated charcoal fabric.

FIGS. 7-9 depict the surfaces of a knitted activated-charcoal fabric, a woven fabric and a non-woven, i.e. felt, fabric. The fabrics in FIGS. 7 and 8 are from the same manufacturer. The felt fabric in FIG. 9 is not. All of them comprise activated-carbon fibers of around 8-10 microns in diameter. They are characterized by the same adsorption and absorption properties. It is clear that the knitted fabric of FIG. 7 is the least susceptible to leaving bits of fiber on the treated surface.

Simulated CWA experiments were performed to establish the adsorption characteristics of a test simulated CWA, diethyl phthalate (DEP), from hydrofluoroethers/diethyl phthalate (HFE/DEP) solutions onto selected activated carbon fiber fabrics, and other substrates, such as cotton gauze, the powder from M 291 personal decontamination kits, and granular activated carbon, was done.

Approximately 100 ml of a 0.01% solution of DEP and an HFE solvent was pre-pared in a 120-ml glass jar. These samples initially contained approximately 0.015 g of DEP.

A pre-weighed substrate was placed in the 0.01% DEP/HFE solution, capped, and immediately placed on the two-roll mill, agitating the solution for five minutes. After 5 minutes, an aliquot of the solution was analyzed by UV. The sample was placed back on the industrial roller, and the sampling procedure was repeated at various time intervals.

Tests were performed with 0.01 wt-% solutions of DEP in the four solvents listed above with the various substrates listed in Table 2-1. The ratio of the weight of adsorbent used to the initial weight of contaminant in solution was examined at various levels.

TABLE 2-1

Substrates Examined

| Brand | Model NO: | Lot #: |
|---|---|---|
| KoTHmex Activated Carbon Fabric | AW1101 | 6111796-04 |
| KoTHmex Activated Carbon Fabric | AW1501 | 610309R |
| KoTHmex Activated Carbon Felt | AM1131 | 87112605 |
| KoTHmex Activated Carbon Felt | AM1132 | 8809>>-08 |
| Activated Powder from M 291 Kit | M 291 Skin Decontamination Kit | |
| Norit Granular Activated Carbon | GAC 1240 | |
| Kendall Curity Cotton Gauze Sponges | USP Type VII Gauze | 2634 |

TABLE 2-2

Specifications of KoTHmex Activated Carbon

| Item | AW1501 | AW1101 | AM1131 | AM1132 |
|---|---|---|---|---|
| Surface area ($m^2$/g) | 1500 | 1100 | 1100 | 1100 |
| Total pore volume (ml/g) | 0.7~0.8 | 0.5~0.6 | 0.5~0.6 | 0.5~0.6 |
| Average pore Dia. (Å) | 19~20 | 19~20 | 19~20 | 19~20 |
| Fabric weight (g/$m^2$) | 70 ± 5 | 100 ± 5 | 192 ± 20 | 250 ± 20 |
| Fabric thickness (mm) | 0.35~0.45 | 0.4~0.5 | 2.0~0.25 | 2.75 ± 0.25 |
| Fabric width (cm) | 100 ± 2 | 100 ± 2 | 117 ± 2 cm | 117 ± 2 cm |

The concentration of DEP in the HFE solutions was determined by measuring the adsorption of UV light at a wavelength of 274 nm by a test sample in a 10 mm cell. DEP exhibits a significant adsorption peak at this wavelength, while the HFE's are transparent.

Initial UV baselines of pure, uncontaminated, HFE solvents were taken before each run. All runs are compared to the pure HFE solvents at a wavelength of 274.

An initial UV measurement of the 0.01% DEP/HFE solution was taken before any substrate was added to the sample.

The adsorption characteristics of DEP from solution in the various solvents onto a single substrate (AW 1101 fabric) were first examined to determine which solvent had the most promising properties. These results are presented in FIG. 1.

As can be seen from FIG. 1, the adsorption characteristics of DEP from DEP/HFE-7100 and DEP/HFE-7200 solutions are comparable onto the AW1101 fabric at one loading level. The rate and extent of DEP from solution in HFE-7500 and the 80/20 7200/7500 mixtures are lower than from solution in HFE-7100 and HFE-7200. FIGS. 5-1 is a comparison of HFE-7200 and the 80/20 7200/7500 mixtures at different loading levels for the first five minutes of contact time. This figure indicates that DEP adsorbs more readily from HFE-7200 than from the 80/20 mixture at all loading levels.

Time line adsorption data were collected for the adsorption of DEP from HFE-7200 with various substrates of interest at three different substrate/initial contaminant levels (20, 60, 200 gr./gr.). The initial adsorption rates are of particular importance since, in actual decontamination simulations, there will not be much time available for decontamination.

FIGS. 5-2 compares the percent DEP remaining after the first 5 minutes of contact for the different substrates at different loading levels. With all substrate specimens, the percentage removal of DEP increases as the loading levels increase to 200 g activated carbon substrate per gram of DEP.

The DEP removal levels of the AW1501 fabric and AM1131, and AM1132 felt are comparable to that of the powder from the M291 decontamination kits. All four substrates removed over 99% of the contaminant at loading levels of 100 gr/gr.

A 4"×4" sample of substrate was suspended freely by a nylon fishing line from a zeroed Mettler electronic balance. The initial weight of the substrate was recorded. The substrate was then allowed to soak in a bath of HFE-7200 until completely saturated. The HFE-7200 bath was removed from the substrate and allowed to drain while recording the weight of the HFE-soaked substrate over time. This procedure was repeated for various substrates.

The results are presented in FIG. 1, which presents the weight of solvent retained per weight of substrate as a function of time. Except for the carbon felts, liquid retention was less then 2 gr./gr. after 100 sec (1.5 minutes). After 300 sec (5 min), the felts still retained between 3-5 gr./gr., whereas zero retention was observed for the other substrates.

Liquid retention is greater in the AM1131 and AM1132 felts than in the other substrates tested. Two mechanisms of the liquid loss are encountered: liquid drainage and evaporation. In the AW1101 fabric, for example, the liquid drainage is encountered in the first 50 seconds, after which there is a sharp bend in the curve. This sharp bend corresponds to the evaporation of the liquid from the substrate. In the AM1131 and AM1132, evaporation does not does not become dominant until 150 seconds after the removal of the solvent bath from the substrate. Liquid is retained in the felts for a period of 900-1200 second (15-20 min), but only 2-3 minutes in the other substrates. Fabrics do not provide pockets for the liquid to accumulate, however, the felts do, allowing liquid retention to be greater.

A method of decontamination of a surface with a solvent saturated adsorbent pad system involves the following steps.

1. Removal of the bulk of the CWA from the contaminated surface by mechanically scouring with the adsorbent pad.
2. Removal of traces of CWA from the contaminated surface by chemical dissolution in minimal amounts of the solvent.
3. Diffusional transport of agent to the active sites on the adsorbent through the solvent.
4. Adsorption of the agent onto the active sites.
5. Storage of the adsorbent pad in a sealable bag for subsequent disposal.

To decontaminate personnel with this type of a process, an appropriate adsorbent pad needs to be developed.

A series of decontamination tests were performed to compare the relative contaminant removal effectiveness of different decontamination processes and materials.

The decontamination tests were performed with pieces of meat that were purchased from local supermarkets. These included pork skin, pork chops, pork fat, beefsteak, and chicken skin. Most of the tests were performed with pork skin and with pork chops.

The experiments were performed with neat and polymer thickened diethyl phthalate (DEP), to which 5 wt-% of a fluorescent tracer dye, TRY-33 from Day-Glo Company, was added. The physical properties of DEP are similar to those of Agent VX, and it is often used as a VX simulant. Because of the presence of the dye, the mixture glows a bright green color when illuminated by ultraviolet light (@ 364 nm), rendering it easily visible.

The neat simulant has a viscosity of approximately 1.23 cp. The thickened simulant, which was made by dissolving 3 wt-% of Paraloid K-125 acrylic polymer (Rohm & Haas Co.) to the neat simulant, has a viscosity of approximately 35 cp. This value is consistent with reported values for thickened CWA agents.

Contaminant was applied to a test substrate by spraying a dilute solution of contaminant in a volatile solvent against the substrate, and allowing the solvent to evaporate.

The solvent of choice was Vertrel MCA+ (Du Pont Co.). Vertrel MCA+ dissolves both neat and thickened simulant, and is very volatile, boiling at 36° C. It is also non-flammable and safe to use in a well-ventilated area.

The amount of contaminant added to a substrate was established by the characteristics of the spray dispenser, the concentration of simulant in the liquid being sprayed, spraying time, the surface area of the substrate, and the relative position of the dispenser and substrate.

Initially, when relatively high surface loads of contaminant were being applied, a Misto® olive oil sprayer was used to dispense a 1 wt-% contaminant solution. The Misto® contains a built-in air pump. The compression piston was pushed ten times prior to spraying the solution against the test piece for two seconds. The amount of simulant dispensed solution was measured by spraying contaminant solution onto a tared sheet of aluminum foil for a known period of time, and measuring the weight change after the solvent had evaporated on an analytical balance significantly over the time span of an experiment due to evaporation of volatile products.

In subsequent tests, where more dilute solutions were applied, a more controllable spray system was used. The solutions were pressurized with nitrogen at a pressure of 30 psig, and dispensed through a low capacity Mini-mist spray nozzle (McMaster Carr Co. Cat. No. 3178K81). Different dispensers were used for neat and thickened solutions. The output of the neat dispenser was about 50 grams/minute of solvent. The output of the thickened dispenser was about 45 grams/minute of solvent.

For low-level tests with neat simulant, the contaminant deposition rate was estimated to be 0.002 grams/m$^2$ per second. This value is based on a spraying rate of 50 grams/minute, a contaminant concentration of 63 ppm (determined by UV spectroscopy at 274 nm), an assumed deposition efficiency of 22% (since the test samples were sprayed at 3-4"), and a sample area of 58 cm$^2$ (9 in$^2$). For thickened simulant, the deposition rate was 10% lower because of the slightly lower nozzle output.

As outlined above, fluorescent oil was used as a contaminant in these decontamination studies. Trace levels of this oil are easily detected by eye, or in photographs, when the surface being examined is illuminated with ultraviolet light (364 nm). Pictures are useful for giving a general idea of the cleanliness of the substrate, but a more quantitative comparison was needed in order to differentiate the results. To quantify these observations, a procedure was developed in which photographs of the substrates being processed were digitally analyzed on a personal computer, using Adobe PhotoShop as image analysis software.

A test consisted of the following steps:
a. The uncontaminated sample was photographed with the digital camera under normal light (i.e. with the camera flash lamp), and under UV illumination.
b. The sample was then contaminated by spraying with a contaminant solution of a known concentration for a fixed period of time. This provided an approximate value of the initial level of contamination.
c. The contaminated sample was then photographed under UV illumination.
d. The contaminated sample was then subjected to a decontamination procedure.
e. The decontaminated sample was photographed under UV light and under normal light, as in (a) above.
f. The digital images were then transferred from the camera to a personal computer.

Values of the decontamination factor, DF, were obtained from the histograms of as-taken images. In those runs where a high DF was noted, the auto-enhanced images were examined to estimate low level residues.

Three different decontamination fluids were examined. Deionized (DI) water, 0.5% bleach solution, and 0.5% soap solution (Johnson's Baby Shampoo) were tested. Johnson's Baby Shampoo was used for its mild effect on sensitive areas of the human body.

Experiments were performed at spray pressures of 5 psig, 15 psig, and 30 psig.

The flow rate was varied independently of the pressure by changing the nozzle used on the spray gun.

Spray experiments were performed in 10 second intervals, up to 80 seconds, when required. The spray cleaning procedure was halted after each interval to photograph the to sample and to document the level of decontamination.

The results indicate that the nature of the substrate being decontaminated has a significant effect on the rate and extent of decontamination. A pork skin was harder to decontaminate than a pork chop. Whereas a pork chop was essentially clean after 10 seconds of spraying, significant amounts of contaminant remained on a skin under these circumstances.

As a first estimate, it takes about 30 second to 60 seconds to decontaminate a pork skin. This is a long time, given that the surface area of the contaminated samples is 140 cm$^2$. Prorating this time to the surface area of a human body (2 m$^2$ or 20,000 cm$^2$) results in a calculated patient decontamination time of 4,500 to 9,000 seconds (assuming that only one nozzle is used. Based on a spray pressure of 15 psig, liquid consumption per patient would be of the order of 60 L to 120 L, which is not an insignificant amount. The advantage of a spray system is that an apparatus with a plurality of nozzles could be used. A patient could be placed under a bank of a dozen nozzles, which would reduce the decontamination time twelve-fold. However, the amount of decontamination liquid required would remain the same.

A series of decontamination tests were performed with M-291 personal decontamination kits.

The test pieces were photographed before contamination, after contamination, after being wiped with the M 291 applicator for cumulative periods of time of 10 seconds, 20 seconds, 40 seconds, and 70 seconds. By that time, the test pieces were black, and fairly opaque to both visible and UV light. In an attempt to determine whether contamination still remained on the surface after applying the M-291 kit for 70 seconds, the test pieces were then washed with a low pressure (from 6 psig to 15 psig) water spray for sufficient time to remove most of the adhering powder.

Tests were performed with both dry and liquid soaked cotton wipes and sponges.

A series of tests were performed in which contaminated pork skins were wiped incrementally with dry and liquid-soaked cotton gauze pads. In these tests, the skins were rubbed with a Kendall Curity 4-inch square cotton gauze pad. After the initial set of photographs, additional UV photographs were taken after each of the following steps:

one wiping pass with one outer surface of the pad a second wiping pass with the other outer surface of the pad a third wiping pass with the inner surface of the pad a complete rubbing of the surface with the used pad, which took about 4 to 5 seconds to perform.

As outlined in FIG. 6, tests were performed with dry wipes, and with wipes saturated with the following liquids: HFE-7100, HFE-7200, deionized water, and 0.5% bleach solution.

These results indicate that the contaminant is not removed by simply wiping the surface up to three times, for all the conditions tested. The surface has to be thoroughly rubbed down to have any significant amount of contaminant removal.

In terms of the removal of neat simulant, an HFE-7200 soaked pad more effective than a HFE-7100 soaked, which in turn, was generally more effective than wiping with a dry pad.

One of the characteristics that distinguishes the hydrofluoroethers from aqueous decontamination liquids is that the simulant being tested (and by extension, chemical warfare agents of interest) is soluble in the hydrofluoroethers but not in aqueous solutions.

A number of runs in which the effects of pressing a wet pad against a contaminated pork skin surface on the removal of fluorescent unthickened simulant were examined. These runs were:

| Run No. | Decon Liquid | Adsorbent | Contaminant Level |
|---|---|---|---|
| H-01 | HFE-7200 | Cotton | Low |
| I-01 | HFE-7200 | AC 1102 | Low |
| H-22 | HFE-7200 | Cotton | High |
| H-23 | Water | Cotton | High |
| K-04 | HFE-7200 | AC 1101 | High |

In the above table, the terms cotton, AC 1101, and AC 1102 refer to a Kendall Curity 4 in square gauze pad, and to 4 in square pads made of Kothmex 1101 and 1102 non-woven activated carbon fabrics, respectively. There was no rubbing of the decontamination pad against the surfaces being decontaminated in any of these runs. The objectives were to determine the effects of solubility in the decontamination liquid (DEP being soluble in HFE-7200, and insoluble in water), and of adsorption on the substrate on the rate and extent of decontamination.

At high surface contamination levels, simply pressing with a water saturated cotton pad had essentially no effect. Pressing with an HFE-7200 saturated cotton pad resulted in some contaminant removal, whereas pressing with an HFE-7200 saturated activated carbon fiber cloth resulted in significant removal, with the felt (picture not shown) providing better results than the fabric. The activated carbon fabric is shown to provide a better comparison with the cotton fabric. These runs were performed over a time span of up to 1,000 minutes. At low surface contaminant levels, the contaminant was substantially completely removed in less than one hour (about 10 minutes appears to effective) by HFE-7200.

These results indicate that agent can be removed to very low levels by dissolution in a period of time that would be useful. Removing agent at high levels without applying shear is a slow process even if the agent is soluble in the decontamination liquid. The extent of contaminant removal at high levels is enhanced if it can adsorb on the wipe holding the liquid.

At low contamination levels, the concentration of dissolved contaminant remains low, so that the driving force for dissolution remains high. At high contaminant levels, the concentration of dissolved agent builds up, slowing down the dissolution process. Having an adsorbent wipe increases the rate of contamination removal because the adsorption process lowers the concentration of dissolved contaminant in the decontamination liquid. Thus, an HFE-7200-soaked activated carbon wipe is more effective than an HFE-7200-soaked cotton wipe.

The following characteristics are believed desirable for a decontamination pad: high decontamination liquid retention capability, high contaminant adsorption capacity, and good mechanical properties with minimal fiber shedding when the pad is wiped against the surface being decontaminated.

Kothmex AM 1132 Felt exhibited excellent retention and adsorption properties. however, is fairly friable, and tended to shed when rubbed against a surface. Kothmex AW 1102 cloth mechanical integrity and was much less friable. This pad, shown in FIG. 3-24, consists of a 3.5 inch square piece of AM 1132 felt enclosed in an envelope of AW 1102 cloth.

| Run No | Substrate | Contaminant | Initial Contaminant Level, $g/m^2$ |
|---|---|---|---|
| J-01 | Pork Skin | unthickened DEP | 1.1 |
| J-02 | Pork Chop | Unthickened DEP | 1.1 |
| K-08 | Pork Skin | Thickened DEP | 1.6 |
| K-09 | Pork Chop | Thickened DEP | 1.6 |

In these tests, the contaminated substrate was first wiped with one side of the pad for a period of one minute. The wiping was performed in the photographic booth to take advantage of the UV illumination. The wiped surface was then contacted with the other side (the clean side) of the wipe, in a sealed bag plastic bag to prevent evaporation, for various periods of time of 15 minutes and up in duration, under a pressure of 100 kPa (76 torr). The pressure was applied by placing the plastic bag and its contents between a blood pressure cuff and a one liter bottle, and then pressurizing the cuff with compressed air to the desired pressure of 100 kPa.

Photographs with UV illumination were taken of the uncontaminated substrates, of the contaminated substrates, after wiping for one minute, and after each soak period.

Examination of these sets of figures shows that most of the contamination is removed by the end of the first wipe. In fact, much of the contamination appeared to have been visibly removed during the first few seconds of wiping. Most of the post-wipe residues are removed by a 15-minute soak, with only traces left after a 100-minute soak. It was easier to clean the relatively smooth pigskin than the pork chop, which contained bone and gristle, and thus had a more irregular surface. Thickened contaminant was somewhat more difficult to remove than the unthickened contaminant. A post-soak rub also appeared to be beneficial.

While there was less shedding with the composite pad than with the A/M 1132 felt, some carbon fiber residues were observed on the pork skin.

In order to obtain realistic estimates of the time needed to decontaminate a patient by different procedures, two sets of decontamination tests were performed on a life size mannequin.

The purpose of the first test was to estimate the time needed to decontaminate the head and the outer clothes, and then strip the mannequin following the protocol of FM-8-10-7. The second set of tests examined the amount of time required by, and the effectiveness of, different methods of decontaminating the unclad mannequin.

To provide some degree of realism, the test operators performing these tests were is clad in protective clothing. Each operator wore:

a. Poly-coated Tyvek coveralls, hood, and overboots. This grade of protective clothing is vapor impermeable, and offers protection against hazardous chemicals.

b. Gas Mask. Israeli Simplex gas mask.

c. Rubber Gloves: Heavy duty, 30 mil, 18" neoprene gloves.

d. Rubber apron: 35"×45" neoprene aprons.

While not offering MOPP-4 protection, this ensemble offers more protection than the protective garments that would be worn by most civilian responders in a weapon of mass destruction emergency.

The operators noted that this ensemble degraded their performance in that:

a. the gloves reduced their manual dexterity, b. the gas mask interfered with their ability to communicate (they could not talk to each other) and restricted their peripheral vision, and c. they perspired profusely while wearing the suits, since these tests were run when the ambient temperature was about 80° F. They could not work for more than one hour without resting, and drinking profuse amounts of water.

The test was performed with the mannequin clad as follows:

Outer protective wear: Poly-coated Tyvek coverall, hood, and overboots, Simplex gas mask, and rubber gloves, Normal wear: US Air Force fatigue jacket, US Army battle uniform pants, web belt, combat boots, gloves Underwear: Undershirt, underpants, socks.

The mannequin was laid on a stainless steel wire-rack supported by a polyethylene tub. The working height was 40 in.

The purpose of these tests was to compare the amount of time required by different decontamination methods, and estimate the resulting decontamination efficiencies.

These decontamination tests were performed with the unclad mannequin to which three meat samples were affixed. A 3"×3" pork chop was attached to the chest and 3"×3" pieces of pork skin were attached to the inner thigh and to the back. Before being placed on the mannequin, the sample pieces were photographed under visible and UV light, contaminated by spraying with a 0.1 wt-% solution of thickened DEP in Vertrel MCA+, and photographed again under UV lighting. The initial contamination levels were set at a fairly low level of approximately 0.1 gr./m². After the decontamination test, the samples were photographed under UV lighting and visible light.

In terms of elapsed time, it took approximately four man-minutes to perform one decontamination pass. Spraying with a 15 psi water wand (1-lpm output) took one operator about four to five minutes per body pass. It took two operators about 2 to 2½ minutes to perform a single wiping pass from top to bottom, and about 4 to 4½ minutes to perform two passes, irrespective of whether the wipe was a water soak cotton gauze pad, a bleach soaked sponge, or an HFE-7200 activated carbon fiber pad.

The decontamination levels achieved were erratic, even, as documented by the videotapes, the operators tried to systematically spray clean or wipe the mannequin from head to toe. Decontamination levels ranged from nearly no removal to nearly complete removal, some times with the same method. Even though the operators knew that the meat samples were contaminated, they tried to treat these sample spots in the same manner as the rest of the body. They had no way of telling how well any specific spot was treated, and whether any contaminant was left, other than the post-experiment photographs.

Another issue is that the residual level of contamination estimated from visual inspection of the photographs is much lower than that obtained by photometric analysis. In these instances, the low level of change in fluorescence is due to a high background fluorescence (from the bone in the pork chop) and a low initial level of contamination.

One big obstacle to reducing the time needed to decontaminate a patient, especially a litter patient, is that there are no means available to the decontamination team of determining whether a patient is contaminated, much less pinpointing the contaminated areas. Because the state of contamination of each patient is unknown, all patients have to be stripped and decontaminated from head to toe. If there were a means of determining that only a small specific part of the uniform, or body, was contaminated (for example a hand-held CWA sniffer/alarm device), only that region would have to be decontaminated before the patient could be transported into a "clean" facility without compromising the safety of the individuals in side the facility. There would be no need to strip all patients, which imposes a time tax of at least 10 minutes per patient, and the area that would have to be decontaminated could be reduced by one to two orders of magnitude.

We have developed an absorptive/adsorptive activated carbon fiber wiping pad as a non-agent specific means of decontaminating open-wounds. The pads can be used with minimal amounts of a non-hazardous CWA solvent. The system includes an adsorbent pad and decontamination fluid in a sealed, disposable plastic packet. The decontamination fluid and the adsorbent pads are non-hazardous, nontoxic, and nonflammable, and the proposed system should be inherently safe.

The foregoing description of the illustrative embodiments reveals the general nature of the decontamination system and method. Others of skill in the art will appreciate that applying ordinary skill may readily modify, or adapt, the system and method disclosed without undue experimentation.

The descriptions of the illustrative embodiments are illustrative, not limiting. The method and system have been described in detail for illustration. Variations to the specific details can be made by those skilled in the art without departing from the spirit and scope of the invention.

Descriptions of a class or range useful includes a description of any subrange or subclass contained therein, as well as a separate description of each member, or value in said class.

What is claimed is:

1. A pad for wiping a contaminant from a contaminated surface, said pad comprising;

A. a layer of activated-carbon fabric comprising
   a sheet of knitted activated-carbon fabric,
   one or more sheets of non-woven activated-carbon fabric that are not knitted attached to said sheet of knitted activated-carbon fabric;

B. an impermeable layer attached to said one or more sheets of non-woven activated-carbon fabric; and C. a decontaminant liquid saturating said layer of activated-carbon fabric and acting as a solvent for said contaminant, whereby the sheet of knitted activated-carbon fabric can contact the surface so that the liquid dissolves the contaminants, which are sequestered by the activated carbon.

2. The pad as defined in claim 1 in which the layer of non-woven activated-carbon is a needle punched activated-carbon felt.

3. The pad as defined in claim 1 in which the liquid is a non-aqueous liquid that comprises a hydrofluoroether (HFE).

4. The pad as defined in claim 1 in which the liquid is a non-aqueous liquid that comprises a hydrofluocarbon (HFC).

5. The pad as defined in claim 1 in which the impermeable material comprises at least one of polyethylene and polyvinylidene chloride.

6. A pad for wiping contaminants from a contaminated surface, said pad comprising:
   A. a layer of activated-carbon fabric having a first surface configured to directly contact the contaminated surface, wherein the layer of activated-carbon fabric comprises a layer of knitted activated-carbon fabric attached to a layer of non-woven activated carbon fabric that is not knitted, a surface of the layer of knitted activated carbon fabric arranged as the first surface configured to directly contact the contaminated surface;
   B. a layer of impermeable material over a second surface of the layer of activated carbon fabric opposite to said first surface; and
   C. a decontamination liquid that is an organic solvent for the contaminants, the liquid saturating the layer of activated-carbon fabric;
      wherein the liquid dissolves the contaminants, which are essentially entirely sequestered by the activated-carbon.

7. The pad as defined in claim 6 in which the layer of non-woven activated-carbon is a needle punched activated-carbon felt.

8. A pad for wiping contaminants from a contaminated surface, said pad comprising:
   A. a layer of activated-carbon fabric having a first surface configured to directly contact the contaminated surface, wherein the layer of activated-carbon fabric comprises a layer of knitted activated-carbon fabric attached to a layer of activated carbon fabric that is not knitted, a surface of the layer of knitted activated carbon fabric arranged as the first surface configured to directly contact the contaminated surface;
   B. a layer of impermeable material over a second surface of the layer of activated carbon fabric opposite to said first surface; and
   C. a decontamination liquid that is an organic solvent for the contaminants, the liquid saturating the layer of activated-carbon fabric;
      wherein the liquid dissolves the contaminants, which are essentially entirely sequestered by the activated-carbon.

9. The pad as defined in claim 8 including an impermeable container surrounding said layers and thereby preventing premature evaporation of said decontamination liquid.

10. The pad as defined in claim 8 in which the liquid is a non-aqueous liquid that comprises a hydrofluoroether (HFE).

11. The pad as defined in claim 10 wherein the HFE is selected from the group consisting of: an HFE with chemical formula $C_5F_9H_3O$, an HFE with chemical formula $C_6F_9H_5O$, and an HFE with chemical formula $C_9F_{15}H_5O$.

12. The pad as defined in claim 8 in which the liquid is a non-aqueous liquid that comprises a hydrofluocarbon (HFC).

13. The pad as defined in claim 8 in which the impermeable material comprises at least one of polyethylene and polyvinylidene chloride.

14. The pad as defined in claim 8 in which the contaminated surface is an open wound in human skin.

15. The pad as defined in claim 8 in which the contaminated surface is a surface of a piece of contaminated equipment.

\* \* \* \* \*